United States Patent
Southard et al.

(10) Patent No.: US 11,304,416 B2
(45) Date of Patent: Apr. 19, 2022

(54) CYCLOPENTASILOXANE AND CATIONIC BIOCIDE AS A FORMULATION ADDITIVE TO ENHANCE PERSISTENT SANITIZING AND MISCIBILITY

(71) Applicant: Relevo, Inc, Carmel, IN (US)

(72) Inventors: Jeffrey L. Southard, Windsor, CO (US); Brian K. Southard, Carmel, IN (US)

(73) Assignee: Relevo Labs, LLC, Carmel, IN (US)

( * ) Notice: Subject to any disclaimer, the term of this patent is extended or adjusted under 35 U.S.C. 154(b) by 81 days.

(21) Appl. No.: 16/581,109

(22) Filed: Sep. 24, 2019

(65) Prior Publication Data

US 2020/0093127 A1    Mar. 26, 2020

Related U.S. Application Data

(60) Provisional application No. 62/735,308, filed on Sep. 24, 2018.

(51) Int. Cl.
| | |
|---|---|
| *C11D 3/48* | (2006.01) |
| *A01N 33/12* | (2006.01) |
| *A61Q 17/00* | (2006.01) |
| *A61Q 19/10* | (2006.01) |
| *A01N 55/00* | (2006.01) |

(52) U.S. Cl.
CPC ............. *A01N 33/12* (2013.01); *A01N 55/00* (2013.01); *A61Q 17/005* (2013.01); *A61Q 19/10* (2013.01)

(58) Field of Classification Search
CPC .... C11D 3/43; C11D 9/36; C11D 1/62; C11D 3/162; C11D 3/201; C11D 3/373; C11D 3/3734; C11D 3/48; C11D 3/3927
See application file for complete search history.

(56) References Cited

U.S. PATENT DOCUMENTS

| | | | | |
|---|---|---|---|---|
| 6,248,343 | B1* | 6/2001 | Jampani | A61P 29/00 424/405 |
| 2006/0123562 | A1* | 6/2006 | Ghosh | D06L 1/04 8/147 |
| 2006/0200914 | A1* | 9/2006 | Evers | D06L 1/02 8/142 |
| 2007/0099809 | A1* | 5/2007 | Radomyselski | D06L 1/10 510/285 |
| 2015/0141389 | A1* | 5/2015 | Aliyar | A61P 29/00 514/180 |
| 2018/0055753 | A1* | 3/2018 | Wagner | A61K 8/34 |

* cited by examiner

*Primary Examiner* — Charles I Boyer
(74) *Attorney, Agent, or Firm* — Frost Brown Todd LLC; Nicole M. Tepe

(57) ABSTRACT

A composition for a formulation additive that is water free that can be added to a formulation or other solution to increase its sanitizing persistence capabilities. The composition can include, by weight, from about 20% to about 70% cyclomethicone; from about 16% to about 35% quaternary ammonium salt; from about 16% to about 50% solvent; and from about 0% to about 35% emulsifier.

4 Claims, No Drawings

CYCLOPENTASILOXANE AND CATIONIC BIOCIDE AS A FORMULATION ADDITIVE TO ENHANCE PERSISTENT SANITIZING AND MISCIBILITY

CROSS-REFERENCE TO RELATED APPLICATIONS

This non-provisional application claims priority to provisional application No. 62/735,308, titled "Composition for a Formulation Additive to Enhance Persistent Sanitizing and Miscibility," filed Sep. 24, 2018. Application No. 62/735,308 is also incorporated by reference in its entirety.

FIELD OF INVENTION

This invention relates generally to a composition for a formulation additive that is water free and can be added to a formulation or other solution to give it sanitizing and germ blocking capabilities.

BACKGROUND

Sanitizing substances used as a disinfectant are intended to reduce the risk of exposure to and the spread of germs encountered in day-to-day activities. People of all walks of life use hand sanitizers. Many industries, such as health care and food industries, use sanitizers to kill germs on humans and tools handled by humans.

Although the use of sanitizing hand gels, foams, and sprays, and soaps is well known, a need exists for a composition that when added to a product's formulation will give the formulation a new capability to persistently kill a broad spectrum of germs beyond time points the formulation was previously designed to address, provide superior protection once the formulation has dried, and dry quickly without dehydrating the skin. However, many such quick drying gels, foams, and sprays have compositions that lack germicidal persistence once the antimicrobial agent has evaporated, leave no protective barrier behind, and will dehydrate the skin with frequent use. Alcohol-based hand sanitizers, while extremely quick and effective, have no persistence and will excessively dry the skin and damage inanimate surfaces with frequent use.

Accordingly, the need exists for a composition with persistent germicidal activity that is free of water, adaptable to various products or product formulations when applied as liquids, gels, foams, or sprays, adaptable to formulations that contain water, or are water-free and have various ways the composition can be incorporated into a formulation such that it is miscible, and can inculcate a persistent sanitizing benefit to a non-sanitizing product or enhance the sanitizing persistence of new products under development or retail products. Furthermore, the composition is compliant with the requirements necessary for safe and effective use in healthcare facilities and public schools.

The World Health Organization (WHO) and the Center for Disease Control (CDC) recommend "persistent" antiseptics for hand sanitizers. Persistent activity is defined as the prolonged or extended antimicrobial activity that prevents or inhibits the proliferation or survival of microorganisms after application of the product. The popular alcohol-based hand sanitizers while quick, effective and inexpensive are not persistent sanitizing agents and must be reapplied frequently to maintain antiseptic benefit. This composition when added to an existing sanitizing formulation, purpose designed formulation, or other solution will add persistence to the characteristics of the formulation, bringing it to recommended WHO and CDC criteria.

SUMMARY

Examples described herein include compositions and methods to formulate a waterless composition that when added to a conventional alcohol or alcohol-free based hand sanitizer formulation will be miscible and inculcate an increase in persistent sanitizing and germ blocking capability that meets the persistent activity recommended by WHO and CDC. Furthermore, the composition can be added to non-sanitizing formulations or other solutions and inculcate a persistent sanitizing benefit previously not available. This composition can be useful for sanitizing the hands and other surfaces, can provide enhanced benefits and qualities to which users of sanitizing products are accustom, and can be used like a formulation additive or included as a planned formulation component to achieve germ killing capabilities. In one example, the composition can incorporate components that evaporate quickly, increase miscibility of ingredients, have residual germicidal activity, have a physical protective quality, limit damage to surfaces and dehydration of the skin.

Accordingly, an example can include a persistent germicidal composition for a persistent sanitizing substance, which is added to an existing product formulation, purpose-designed sanitizing formulations, or other solutions, and used in lieu of or in conjunction with traditional handwashing or surface cleaning. The invention can also provide a persistent germicidal solution having broad-spectrum germicidal effect. The invention can further include a method of promoting hygiene. The above noted and other purposes of the present invention will become readily apparent upon further review of the following specification and claims.

In one example, adding the composition to a formulation or solution can enhance the persistent sanitizing capabilities of the formulation by effectively killing 99.9% of germs within the first few minutes. Adding the composition create a physical barrier that repels microbial contaminated moisture. The composition can also leave behind a residual germicide for long-term antimicrobial activity, thereby forming physical and chemical barriers that enhance the formulation's persistent sanitizing capabilities, increasing the miscibility of the additive to the formulation.

An aspect of the invention is a water free composition containing ingredients approved for cosmetic use for use on the skin and other surfaces, comprising a germicidal component of up to about 49.5% by weight, more preferably about 47.5% to about 49% of the total composition by weight percentage. The germicidal component is the active pharmaceutical ingredient (API) such as a germicidal quaternary ammonium salt (hereinafter a QUAT). Preferably, the QUAT may be benzalkonium chloride (BAK) which is composed of C8, C10, C12, C14, C16, and C18 homologs, of which up to 70% are the C12 and C14 homologs. More preferably, the C12 and C14 analogs of benzalkonium chloride because these two homologs have the greater antimicrobial activity and less tissue irritation than the other BAK homologs. Most preferably, the C14 analog of benzalkonium chloride (BAKC14) because it has the greatest antimicrobial activity and the least tissue irritation of any of the BAK homologs. The QUAT is dissolved in an equal amount of solvent such as an alcohol. When alcohol is used as the solvent an emulsifier is also present such that the alcohol is present in an amount of 50% by weight of the BAK. In the composition the alcohol is 49.5% by weight, more preferably about 47.5% to about 49% of the total composition by weight percentage. The alcohol may be ethyl alcohol (EA) or isopropyl alcohol (IPA). The alcohol preferably is anhydrous ethyl alcohol and is 200 proof and is Alcohol denatured, Alcohol SD40 or SD Alcohol 40. More preferably the alcohol is 200 proof, specially denatured with Bitrix, and is Alcohol SD40B or SD Alcohol 40B. Bitrix is a required additive is a product is to be considered for use by children. The emulsifiers are from the class of silicone emulsifiers. For low viscosity free flowing liquids emulsifiers containing Cyclopentasiloxane (and) PEG/PPG-19/19 Dimethicone, or PEG/PPG-19/19 Dimethicone (and) C13-16 Isoparaffin (and) C10-13 Isoparaffin, or PEG-10 Dimethicone are best. For more viscous liquids or solids, silicone emulsifiers containing Dimethicone (and) PEG/PPG-18/18 Dimethicone, or Bis-Isobutyl PEG/PPG-10/7/Dimethicone Copolymer are best. The desired emulsifiers are selected based on the end product specifications, liquid or solid, are added to the composition at amounts of 0.25% to 16%, more preferably 0.5% to 5%, most preferably 0.5%.

Examples also include a method for preparing the composition, comprising the steps of combining at least a portion of the solvent and QUAT to form a base API mixture. The base API mixture is ready to receive the addition of the emulsifier. The base API mixture and emulsifier are mixed to form the functional composition that ensures the rapid, uniform dissolution into the end product formulations.

DETAILED DESCRIPTION OF THE INVENTION

Although the use of sanitizing hand gels, foams, and sprays is well known, a need exists for a composition that when added to new or existing formulations or product solutions will give the formulation or product a new ability to persistently kill a broad spectrum of germs beyond time points previously known, provide superior protection once the formulation or solution has dried, and dry quickly without dehydrating the skin or other surfaces. All alcohol-based hand sanitizers, while extremely quick and effective, have no persistence and will excessively dry the skin and damage inanimate surfaces with frequent use. As a result, it is common to restrict the alcohol content in hand sanitizers to approximately 70 percent. Decreasing the alcohol content has the unwanted effect of decreasing the composition's potency for killing germs and bacteria. Furthermore, many product formulations or solutions that could benefit from enhanced sanitizing capabilities, because by their very nature are designed to mitigate the causes or symptoms of microbial contamination, are products like soaps, cleaners, fabric deodorizers, deodorant, and cosmetics are a few such examples. One solution is to add a composition to the product's formulation or solution that will maintain the product formulation's current capabilities, but provide an enhanced persistent activity over extended time periods, provide a physical barrier to external contaminated moisture sources, and prevent the hands or surface from drying out or damage.

The present invention is directed to a composition for a persistent sanitizing germ block with a bioactive ingredient that is safe and effective in killing germs. When added to a product's formulation or solution it enhances the persistent sanitizing capabilities, dries quickly, does not leave a sticky residue, and does not contribute to dry skin or damaged surfaces. In various embodiments, the present invention is directed to a composition and method of making a composition that persistently kills germs and is gentle to the skin or other surfaces when added to other formulations and solutions. Another feature of this formula is that it does not change the functionality or the way an existing product formulation or solution will be delivered or perform. This invention achieves all these functions with a single composition.

The invention also includes a method of preparing the composition.

One embodiment of the present invention has been shown to kill 99.9% of germs in seconds of administration to common bacterial (germ) cultures. It is a persistent sanitizing composition that is water-free. It is intended for use as an additional composition in a product formulation to convey a sanitizing capability or persistence sanitizing capability to a formulation where none previously existed. It is intended for use in formulations that would be used for products designed to mitigate the undesirable effects of microbial contamination.

Specifically, in a preferred embodiment the sanitizing composition is comprised of a bioactive ingredient with recognized persistent activity to kill germs and bacteria, and cyclomethicone.

In the preferred embodiment the sanitizing composition is comprised of the bioactive ingredient which is a quaternary ammonium salt (QUAT) having anti-microbial and anti-viral properties (anti-germ properties) to kill germs and bacteria, a solvent for dissolution of API, cyclomethicone, and an optional emulsifier.

In embodiments of the invention, the QUAT acting as the bioactive ingredient is selected from the group consisting of benzalkonium chloride, benzethonium chloride, methylbenzethonium chloride, cetalkonium chloride, cetylpyridinium chloride, cetrimonium, cetrimide, dofanium chloride, tetraethylammonium bromide, domiphen bromide and any combination thereof. These QUATs have known persistent anti-bacterial, anti-microbial and anti-viral properties so that they kill microbes, germs, viruses and bacteria both in solution and on hard surfaces. The preferred QUAT is benzalkonium chloride, benzethonium chloride or cetyl pyridinium chloride. More preferred is the QUAT benzalkonium chloride. The especially preferred QUAT is the C14 analog of benzalkonium chloride (BAKC14). The QUAT is present the composition in an amount of up to about 20% by weight, more preferably up to about 18% of the total composition by weight percentage, most preferably up to about 17% by weight.

When present in the composition of the invention as a solvent for the QUAT, the alcohol is anhydrous, preferably may be denatured and more preferably may be 200 proof. The alcohol may be ethyl alcohol or isopropyl alcohol. The concentration of alcohol in the composition means that the alcohol is functionally irrelevant as an antibacterial agent and will not contribute to dry skin or damaged surfaces in the final product formulation. Alcohol is present in the composition in an amount of up to about 50% by weight, more preferably up to about 25% of the total composition by weight percentage, most preferably up to about 17% by weight. The alcohol may be ethyl alcohol (EA) or isopropyl alcohol (IPA). More preferably the alcohol is 200 proof, specially denatured with Bitrix, also known as Alcohol SD40B or SD Alcohol 40B. The optional emulsifier is one from the class of silicone glycerol emulsifiers.

Cyclomethicone is the carrier component of the composition. It is an odorless volatile liquid in which the other components of the sanitizing composition are mixed. Upon application to the skin, cyclomethicone and alcohol expeditiously evaporates allowing the QUAT to remain and provide residual germicidal activation with no drying of the skin. This carrier is present in the composition at a concentration by weight up to 70% by weight, preferably from about 50% by weight of the total composition. The preferred cyclomethicone is the cyclomethicone D5 analog also known as cyclopentasiloxane. Other suitable carriers include Alkyl Polymethylsiloxane and isododecane.

To achieve the persistent sanitizing enhancement in a non-sanitizing or non-persistent sanitizing formulation, the composition should comprise of up to about 5% by weight, preferably about 0.5% to about 3%, more preferably about 0.13% to about 0.8% of a product's total formulation by weight percentage.

In an embodiment, the composition is comprised of one or more QUATs, cyclomethicone as a carrier and solvent for dissolution of the QUATs.

The composition can also utilize other persistent microbicides either alone or in combination with the QUATS to further broaden the sanitizing efficacy and persistence. Polyhexamethylene biguanide (PHMB) and Triclosan are examples of other non-QUAT microbicides capable of persistently killing germs, bacteria and viruses.

Thus, an aspect of the present invention is that more than one germicide may be combined for an additive effect in killing germs and bacteria. The germicide components may be used in total (combined) amounts that range up to 40% percent by weight of the composition.

Thus, a single or blended germicide component with known persistent activity is used in the composition and added to an existent non-sanitizing or sanitizing formulation or a purposely designed new formulation for the various embodiments of the present invention. Most conventional hand sanitizers contain only one germ killing agent, typically isopropyl alcohol or commercial grade ethyl alcohol, and have non-persistent activity.

Other features of adding a composition containing one or more QUATS or non-QUATS as the bioactive ingredient to a formulation are its expanded effectiveness as surface sanitizers.

The following are five exemplary compositions in accordance with the present invention with and without the optional emulsifier, and with single and multiple microbicides:

Composition No. 1

| Components | Weight Percent |
| --- | --- |
| Cyclomethicone | 49 |
| Benzalkonium chloride C14 | 17 |
| Alcohol SD40B | 17 |
| Emulsifier | 17 |
| TOTAL | 100% |

Composition No. 2

| Components | Weight Percent |
| --- | --- |
| Cyclomethicone | 66 |
| Benzalkonium chloride C14 | 17 |
| Alcohol SD40B | 17 |
| TOTAL | 100% |

Composition No. 3

| Components | Weight Percent |
| --- | --- |
| Cyclomethicone | 32 |
| Benzalkonium chloride C14 | 17 |
| QUAT | 17 |
| Alcohol SD40B | 17 |
| Emulsifier | 17 |
| TOTAL | 100% |

Composition No. 4

| Components | Weight Percent |
| --- | --- |
| Cyclomethicone | 32 |
| Benzalkonium chloride C14 | 17 |
| PHMB | 17 |
| Alcohol SD40B | 17 |
| Emulsifier | 17 |
| TOTAL | 100% |

Composition No. 5

| Components | Weight Percent |
| --- | --- |
| Cyclomethicone | 31 |
| Benzalkonium chloride C14 | 17 |
| Triclosan | 18 |
| Alcohol SD40B | 17 |
| Emulsifier | 17 |
| TOTAL | 100% |

In one embodiment of the present invention and as seen in Compositions 1 above, the composition contains the following percentages by weight Cyclomethicone at 49%, Benzalkonium chloride C14 at 17%, Alcohol at 17%, and Emulsifier at 17%.

In one embodiment of the present invention and as seen in Compositions 2 above, the composition contains the following percentages by weight Cyclomethicone at 66%, Benzalkonium chloride C14 at 17%, and Alcohol at 17%.

In one embodiment of the present invention and as seen in Compositions 3 above, the composition contains the following percentages by weight Cyclomethicone at 32%, Benzalkonium chloride C14 at 17%, second QUAT at 17%, Alcohol at 17%, and Emulsifier at 17%.

In one embodiment of the present invention and as seen in Compositions 4 above, the composition contains the following percentages by weight Cyclomethicone at 32%, Benzalkonium chloride C14 at 17%, PHMB at 17%, Alcohol at 17%, and Emulsifier at 17%.

In one embodiment of the present invention and as seen in Compositions 5 above, the composition contains the following percentages by weight Cyclomethicone at 31%, Benzalkonium chloride C14 at 17%, Triclosan at 18%, Alcohol at 17%, and Emulsifier at 17%.

In one embodiment of the present invention the formula combines one or more of the bioactive ingredient and alcohol together creating a base API mixture. The emulsifier is then added to the base API mixture and blended. As a final step, the cyclomethicone is added to complete the composition and mixed, ready to be incorporated into a formulation.

The advantage of this method is to create a precise blending process of the ingredients that provide uniform distribution of ingredients, accurate measurement of the API, and create an emulsion to prevent separation in variety of formulations.

In one embodiment of the present invention, the composition can be packaged in small bottles and a specified amount of the composition can be added to an existing retail product with an eye dropper to achieve a sanitizing benefit.

In one embodiment of the present invention the composition is pre-packaged in pre-measured polymeric substances like polyvinyl alcohol packets similar to dissolving dishwashing and laundry detergents packets. Or plastic or foil pouches that can be poured into a solution or formulation to achieve a sanitizing benefit.

Alternatively, the composition may be applied as a standalone concentrate as an aerosol, pump spray bottle or other suitable dispensing method.

In another alternative, the composition may be applied as a standalone concentrate using a squeeze bottle. The plastic squeeze bottle has a narrow mouth or small orifice for dispensing the sanitizing composition contained within the bottle.

This invention has been described in detail with particular references to certain embodiments. The above examples and embodiments should be considered to be illustrative and no way limiting of the present invention. Thus, while the description above refers to particular examples, and embodiments, it will be understood that many modifications may be made without departing from the spirit thereof.

What is claimed is:

1. A composition, that can be added to another formulation or solution and creates a new formulation that is suitable for use on human skin and other surfaces consisting essentially of:
    (a) from about 16% to about 35% by weight of a first germicide, said first germicide being a C14 analog of benzalkonium chloride (BAKC14);
    (b) cyclopentasiloxane at a concentration of 30 to 70% by weight;
    (c) a solvent selected from ethyl alcohol or isopropyl alcohol at a concentration up to 17%; and
    (d) up to about 35% by weight of silicone glycerol.

2. The composition of claim 1, wherein the solvent is essentially anhydrous and 200 proof ethanol, further comprising the additive Bitrix.

3. The composition of claim 1, further comprising (e) a second germicide, wherein the second germicide is a germicidal quaternary ammonium salt (QUAT) or non-QUAT.

4. The composition of claim 3, wherein the second germicide is a non-QUAT Polyhexamethylene biguanide (PHMB) or Triclosan.

* * * * *